US011284851B2

(12) United States Patent
Madabhushi et al.

(10) Patent No.: US 11,284,851 B2
(45) Date of Patent: Mar. 29, 2022

(54) DIFFERENTIAL ATLAS FOR IDENTIFYING SITES OF RECURRENCE (DISRN) IN PREDICTING ATRIAL FIBRILLATION RECURRENCE

(71) Applicant: Case Western Reserve University, Cleveland, OH (US)

(72) Inventors: Anant Madabhushi, Shaker Heights, OH (US); Thomas Atta-Fosu, Cleveland Heights, OH (US); Soumya Ghose, Niskayuna, NY (US)

(73) Assignee: Case Western Reserve University, Cleveland, OH (US)

( * ) Notice: Subject to any disclaimer, the term of this patent is extended or adjusted under 35 U.S.C. 154(b) by 510 days.

(21) Appl. No.: 16/361,421

(22) Filed: Mar. 22, 2019

(65) Prior Publication Data

US 2019/0290233 A1 Sep. 26, 2019

Related U.S. Application Data

(60) Provisional application No. 62/647,206, filed on Mar. 23, 2018.

(51) Int. Cl.
*A61B 6/00* (2006.01)
*A61B 6/03* (2006.01)
(Continued)

(52) U.S. Cl.
CPC .............. *A61B 6/503* (2013.01); *A61B 6/032* (2013.01); *A61B 6/463* (2013.01); *G16H 50/30* (2018.01);
(Continued)

(58) Field of Classification Search
CPC ......... A61B 6/503; A61B 6/032; A61B 6/463; A61B 5/361; A61B 2018/00577;
(Continued)

(56) References Cited

U.S. PATENT DOCUMENTS

2016/0196647 A1* 7/2016 Madabhushi .... G01R 33/34084
382/131

OTHER PUBLICATIONS

Varela et al. 2017 Frontiers in Physiology 8 paper 68 12 pages (Year: 2017).*

(Continued)

*Primary Examiner* — Keith M Raymond
*Assistant Examiner* — Patrick M Mehl
(74) *Attorney, Agent, or Firm* — Eschweiler & Potashnik, LLC

(57) ABSTRACT

Embodiments access a set of radiological images acquired from a population of subjects, where a member of the set of radiological images includes a left atrium (LA) region; construct a statistical shape differential atlas from the images; generate a template LA model from the statistical shape differential atlas, where the template LA model includes a site of interest (SOI); acquire a pre-ablation radiological image of a region of tissue in a patient demonstrating atrial fibrillation (AF) pathology; generate a patient LA model from the pre-ablation image; compute a deformation field that registers the SOI to the patient LA model using deformable registration; compute a patient feature vector based on the deformation field; generate an AF probability score for the patient based on the feature vector; generate a classification of the patient based, at least in part, on the AF probability score; and display the classification or the AF probability score.

20 Claims, 13 Drawing Sheets

(51) Int. Cl.
*G16H 50/20* (2018.01)
*G06N 20/00* (2019.01)
*G16H 10/60* (2018.01)
*G16H 30/40* (2018.01)
*A61B 5/361* (2021.01)
*A61B 18/00* (2006.01)
*G16H 50/30* (2018.01)

(52) U.S. Cl.
CPC ............... *A61B 5/361* (2021.01); *A61B 6/469* (2013.01); *A61B 6/5217* (2013.01); *A61B 6/54* (2013.01); *A61B 2018/00351* (2013.01); *A61B 2018/00577* (2013.01); *G06N 20/00* (2019.01); *G06T 2207/30048* (2013.01); *G16H 10/60* (2018.01); *G16H 30/40* (2018.01); *G16H 50/20* (2018.01)

(58) Field of Classification Search
CPC ............ A61B 2018/00351; A61B 6/54; A61B 6/5217; A61B 6/469; A61B 2090/376; A61B 2034/105; A61B 34/10; A61B 6/504; A61B 2018/00363; G06T 2207/30048; G06N 7/005; G06N 20/10; G06N 20/20; G06N 5/003; G06N 20/00; G16H 50/50; G16H 50/70; G16H 50/30; G16H 50/20; G16H 10/60; G16H 30/40
See application file for complete search history.

(56) References Cited

OTHER PUBLICATIONS

Ghose et al. 2017 Scientific Reports 7 paper 15829 8 pages (Year: 2017).*
Rusu et al. 2017 Scientific Reports 7 paper 41261 11 pages (Year: 2017).*
Atta-Fosu et al. 2021 BMC Med. Imaging:21 paper 45 12 pages (Year: 2021).*
Ghose et al. "Prostate Shapes on Pre-Treatment MRI Between Prostate Cancer Patients Who Do and Do Not Undergo Biochemical Recurrence Are Different: Preliminary Findings." Scientific Reports, 7: 15829 | DOI:10.1038/s41598-017-13443-8. Published on Nov. 20, 2017.
Ourselin et al. "Robust Registration of Multi-Modal Images: Towards Real-Time Clinical Applications." T. Dohi and R. Kikinis (Eds.): MICCAI 2002, LNCS 2489, pp. 140-147. Published in 2002.
Rueckert et al. "Nonrigid Registration Using Free-Form Deformations: Application to Breast MR Images." IEEE Transactions on Medical Imaging, vol. 18, No. 8, Aug. 1999.

* cited by examiner

700

---

Given Patient model $P$, Template model $T$ and SOI $S$, compute and return patient feature vector $x$

---

1: function $\text{SOIF}_{\text{EATURE}}(P, T, S)$

2:    Deformable Registration: Compute optimal F that registers $T$ to $P$

3:    Initialize array for displacement norms and curl:

4:    $Arr1 = [0,...,0]_{N \times 1}, Arr2 = [[0, 0, 0], ..., [0, 0, 0]]_{N \times 3}$ 5:    for $j = 1$ to $N$ do

6:        Find $\mathbf{F}_j$, where $\mathbf{F}_j$ is the displacement vector at $\mathbf{v}_j \in S$ 7:        $Arr1[j] = d_j$ (See 1)

8:        $Arr2[j,:] = \mathbf{c}_j$ (See 2)

9:    end for

10.   $x$ collects the minimum, mean, maximum, and standard deviations of $Arr1$ and $Arr2$.

11:   return $x$

12: end function

DIFFERENTIAL ATLAS FOR IDENTIFYING SITES OF RECURRENCE (DISRN) IN PREDICTING ATRIAL FIBRILLATION RECURRENCE

REFERENCE TO RELATED APPLICATIONS

This Application claims priority to U.S. Provisional Application No. 62/647,206 filed on Mar. 23, 2018, the contents of which are hereby incorporated by reference in their entirety.

FEDERAL FUNDING NOTICE

This invention was made with government support under the grant(s) CA199374, CA202752, CA208236, CA216579, and CA220581 awarded by the National Institutes of Health; and grants W81XWH-15-1-0558, W81XWH-18-1-0440, and W81XWH-16-1-0329 awarded by the Department of Defense. The government has certain rights in the invention.

BACKGROUND

Atrial Fibrillation (AF) is a common cardiac arrhythmia in which rapid and irregular electrical atrial activation causes loss of synchronized contraction of the atria. Potential consequences of AF include symptoms from the rapid and irregular conduction to the ventricle, loss of atrioventricular synchrony, and risk of thromboembolic complications, such as stroke. Rhythm control of AF typically centers on suppression with antiarrhythmic drugs or catheter ablation, the latter primarily directed toward isolation of the pulmonary vein ostia, where initiating triggers have been observed. For persistent or long-standing persistent AF, the success of ablation can be limited: up to 80% of these patients may experience recurrence within a year, and for this population there is controversy over whether additional substrate ablation should be performed beyond pulmonary vein isolation. Consequently, improved prediction of the likelihood of recurrence from pre-ablation contrast-enhanced computed tomography angiogram (CE-CTA) scans, which may aid in patient selection for ablation and in procedure and post-procedure planning, would be advantageous.

BRIEF DESCRIPTION OF THE DRAWINGS

The accompanying drawings, which are incorporated in and constitute a part of the specification, illustrate various example apparatus, methods, and other example embodiments of various aspects of the invention. It will be appreciated that the illustrated element boundaries (e.g., boxes, groups of boxes, or other shapes) in the figures represent one example of the boundaries. One of ordinary skill in the art will appreciate that in some examples one element may be designed as multiple elements or that multiple elements may be designed as one element. In some examples, an element shown as an internal component of another element may be implemented as an external component and vice versa. Furthermore, elements may not be drawn to scale.

FIG. 7 illustrates a method for computing a patient feature vector.

DETAILED DESCRIPTION

Figure 1:
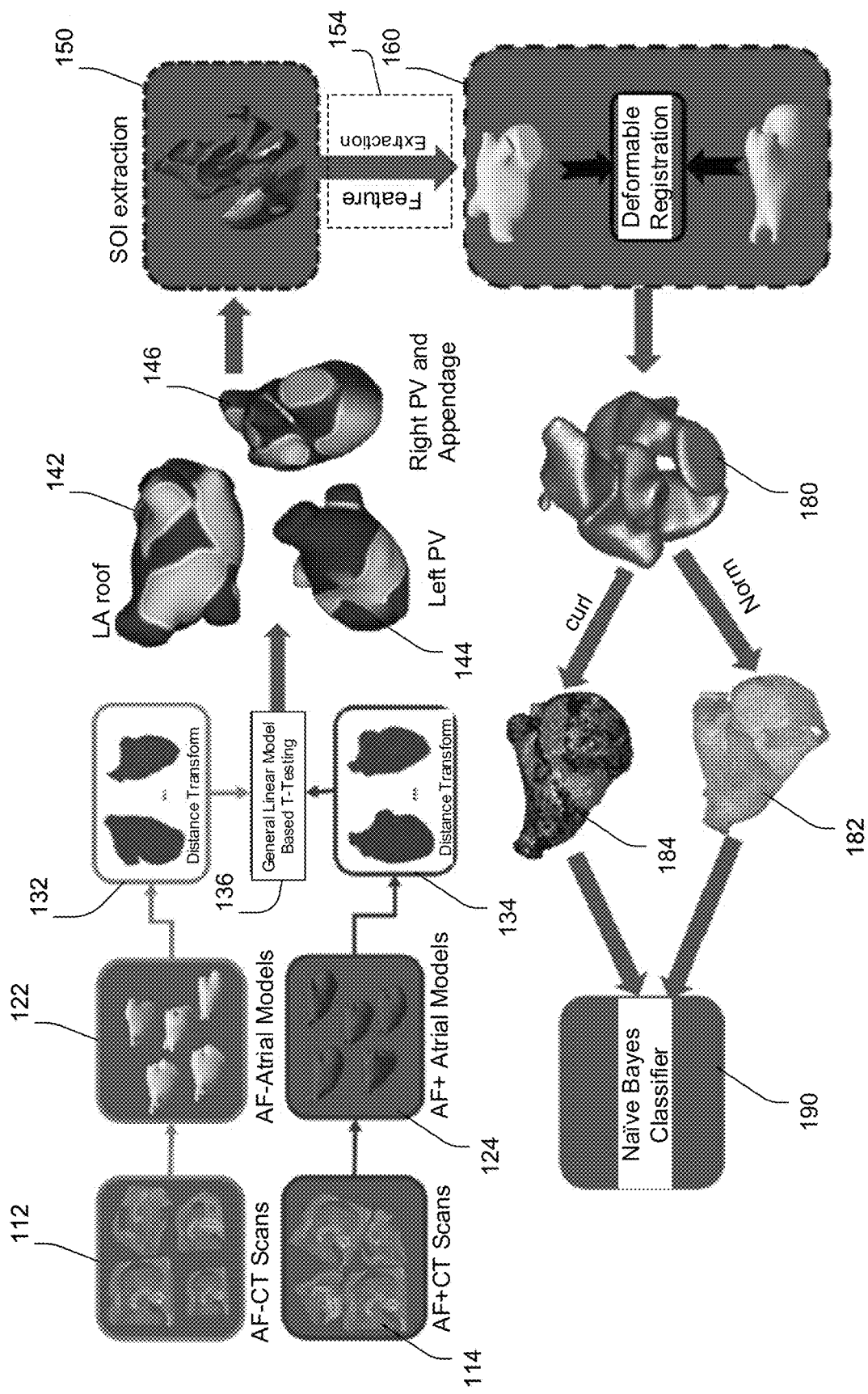
FIG. 1 illustrates a workflow diagram for classifying a patient as likely to experience atrial fibrillation (AF) recurrence post-ablation according to embodiments described herein.

Variations in left atrium (LA) shape and volume may be related to patient prognosis and outcome, including likelihood of atrial fibrillation (AF) recurrence. LA structures may show differences in volume and shape when comparing at-risk AF positive (AF+) and AF negative (AF−) populations. Embodiments employ data acquired using contrast-enhanced computed tomography angiography (CE-CTA) of AF+ patients (i.e., those who experienced AF recurrence) and AF− patients (i.e., those who did not experience AF recurrence). The data is combined into a statistical shape atlas. A statistical shape atlas includes a subgroup of population studies as a shape representation. Statistical shape atlases combine shape information from multiple subjects into one unified representation. Embodiments generate a quantification of differences between different statistical shape atlases, or between an image of a region of tissue of a patient demonstrating AF pathology, and a statistical shape atlas. Embodiments may generate the quantification of differences by identifying and characterizing differences in the shape of the LA. Embodiments use differences in the shape of the LA to distinguish a patient who is likely to experience AF recurrence, from a patient who is unlikely to experience AF recurrence. Embodiments thus facilitate predicting AF recurrence post-ablation therapy in patients demonstrating AF pathology.

Embodiments identify and extract features from medical imagery, including CE-CTA imagery, of identified sites that are predictive of AF recurrence. Embodiments construct a statistical shape differentiation atlas to identify sites of the atrial anatomy that show significant differences in shape or local morphology between AF+ and AF− patients. Embodiments compute features based on the diffeomorphic characteristics within the sites of recurrence identified by the statistical shape analysis, and create a feature map for AF+ and AF− patients, respectively.

Embodiments identify sites of spatial and morphological differences in the LA shape between AF+ and AF−, referred to as sites of interest (SOI). Embodiments compute features based on diffeomorphic properties of a patient's SOI. These features, including magnitude of deformation, quantify diffeomorphic changes in LA anatomy, and changes in the configuration of structures, including pulmonary veins (PV), in AF patients. Embodiments employ a shape differential interrogation approach to identify SOIs on a template atrial model. Embodiments transform annotated atrial shapes into a distance transform representation that encodes atrial boundaries. Embodiments compute a general linear model (GLM) based test to construct the SOI. Embodiments extract features using an optimal deformation field produced by a B-spline registration of the template SOI to a patient's SOI. Embodiments generate a feature vector based on the magnitude of the deformation field and the curl of the deformation field, and characterize the patient based on the feature vector.

One implementation of embodiments is now discussed in greater detail. FIG. 1 is a workflow diagram of embodiments. Embodiments access a set of AF− CT imagery, at 112. Embodiments access a set of AF+ CT imagery at 114. Embodiments identify an SOI, at 150, through an initial atlas creation based on segmented LA masks 122, and 124, of AF+ and AF− patient CT imagery, respectively, followed by a GLM-based t-testing 136 of the SOI 142, 144, and 146 using the distance transform of atlases 132 and 134. Feature extraction includes computing an optimal deformation field 180 between a template SOI and a patient SOI. Embodiments evaluate the curl of the deformation field and the magnitude of the deformation field to generate a feature vector. The feature vector may be provided to a classifier, including, for example, a naïve Bayes classifier illustrated at 190. In other embodiments, other types of classifiers, including machine learning classifiers, may be employed. For example, in one embodiment, the feature vector may be provided to a classification and regression tree based classifier that creates a meta-classifier from at least two weak (i.e., short depth) learners using an aggregation score.

Embodiments construct an LA model from CT imagery. AF− atrial models may be constructed at 122. AF+ atrial models may be constructed at 124. Embodiments segment the LA from non-LA tissue represented in CT imagery. Embodiments may segment the LA from non-LA tissue using a semi-automated or automated segmentation technique. Embodiments may clip pulmonary veins and the left atrial appendage to obtain a final segmentation of the atrial body. The pulmonary veins may be clipped a threshold distance from the ostia. In one embodiment, the threshold distance is three cm.

Figure 13:
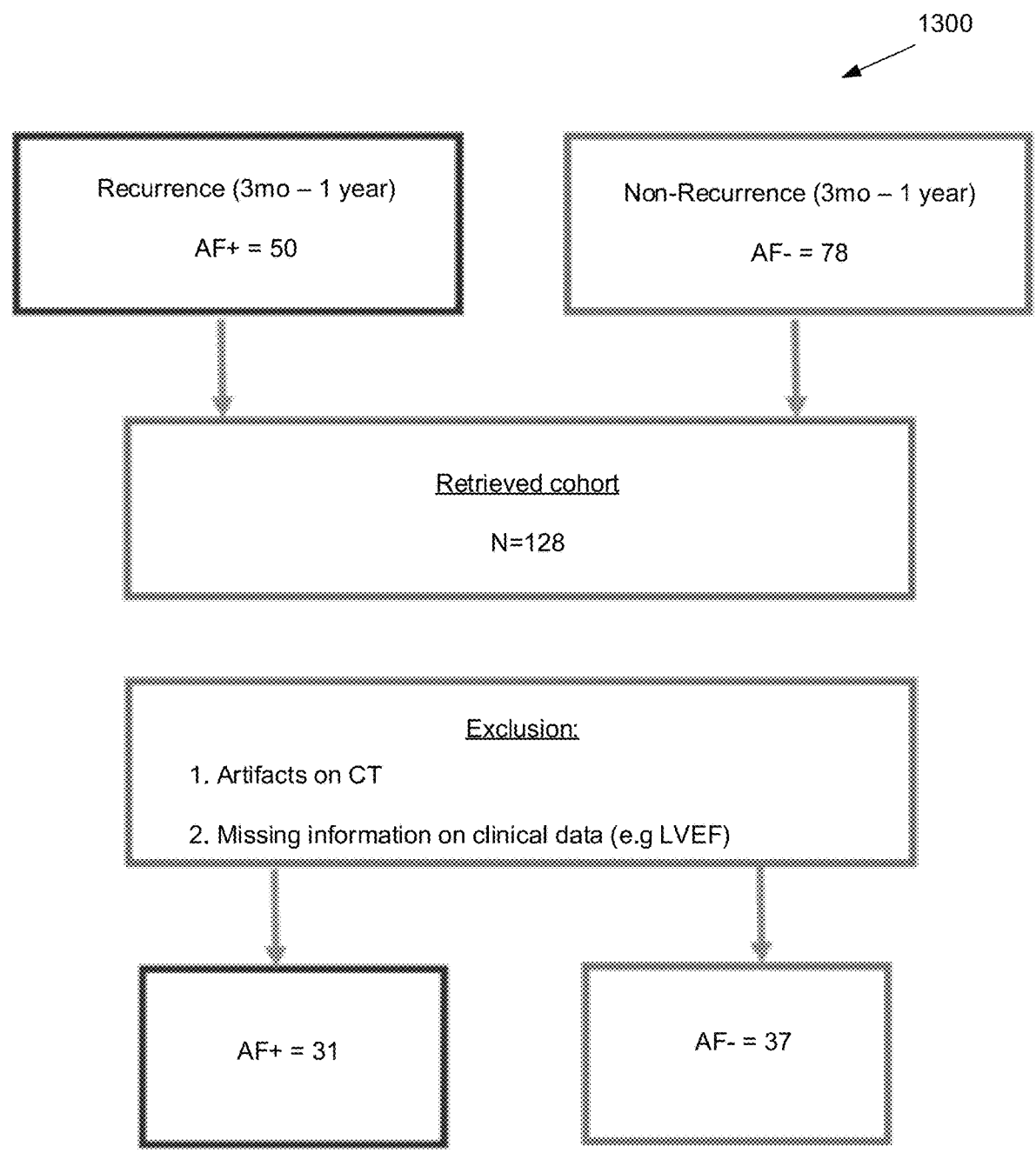
FIG. 13 is a flow diagram of patient cohort selection.

To construct the representative atlas, embodiments access a set of CT imagery of patients who experienced early AF recurrence (e.g., AF+ CT imagery 114), and of patients who did not experience early AF recurrence (e.g., AF− CT imagery 112). In one embodiment, a cohort of sixty-eight patients was selected with a diagnosis of atrial fibrillation who had failed medical management for ablative therapy between July 2015 and November 2016. Non-contrast chest CT was obtained prior to pulmonary vein isolation via radio frequency-ablation or cryo-ablation, and follow-up occurred within 3-12 months of ablation. Recurrence of atrial fibrillation is defined as either recurrence of associated symptoms or evidence of recurrence based on ECG or continuous monitoring. Embodiments may select a balanced set of 15 random samples each from the AF+ and AF− groups, where the template atrial atlas is taken as the AF− patient atrium having the median volume. In other embodiments, other numbers of patients, or sets of random samples from the AF+ and AF− groups, may be selected. FIG. 13 illustrates an example workflow 1300 for selecting patients for analysis and generation of SOIs and statistical shape atlases according to embodiments.

Embodiments select the LA with the median volume T+ for patients in the cohort with early AF (AF+) recurrence. Embodiments also select the LA with median volume T− and for patients in the cohort without early AF (AF−) recurrence. All patients with early recurrence are registered to the T+ template to create an AF+ atlas. All patients with late recurrence are registered to the T− template to create an AF− atlas. Embodiments employ a block matching technique to determine transformation parameters for affine registration. The affine registration of the moving image to the reference image is followed by a B-spline based non-rigid segmentation scheme. Segmented LA masks are employed to constrain the registration within the volume of interest. The segmented LA masks are given the same transformation as the registered images to bring the LA masks and surfaces into correspondence.

Embodiments generate an SOI. The SOI may have a plurality of mesh points. To perform a statistical comparison of the LA shape between AF+ and AF− atlases, atrial masks from the AF+ group are registered to the AF− atlas. All registered LA surfaces of both the early and late recurrence groups are isotropically scaled to 1 $mm^3$ resolution and transformed into a signed distance function. An implicit representation of the LA surface is provided with the signed distance representation and enabled a t-test based comparison of the shape via a non-parametric General Linear Model (GLM) based t-test framework, illustrated at 136. Embodiments quantify statistically significant shape differences of the LA surfaces with, in one example, 5000 random permutation testing, with p-value being corrected for multiple comparisons. Significant shape differences between AF+ and AF− cohorts are then identified as constituting the SOI. Embodiments may identify and compute CT derived features corresponding to the shape of the left atrial appendage and pulmonary veins for predicting likelihood of AF recurrence post-ablation.

Using the implicit shape representation of the balanced set, sites on the atrial surface that had statistically significant ($p<0.01$) local morphological difference between the two groups are identified as the SOI. These sites included the regions around and between the pulmonary vein ostia of both left and right PVs (typically, these are the target sites of surgical ablation). Other significant sites included the regions around the base of the left atrial appendage. These statistically significant sites are projected onto the representative atrial atlas, and then visualized as red-colored surface patches in FIG. 1 at 142, 144, and 146, and in FIG. 2 at 210.

Embodiments generate features based on statistical descriptors of the magnitude and curl of the deformation field for registering the template atlas to a patient's LA model. To simplify notation, we define $S=\{v|v \text{ is in SOI}\}$. Embodiments register a template atrium to a patient atrium using deformable registration techniques, as shown at FIG. 1, 160. The feature extraction phase uses the atria models that have been registered to a common reference coordinate during the construction of the SOI at 150. The diffeomorphometric features are based on the elastic distortion of the template from the patient's atria. Embodiments perform a deformable registration of the template to each of the individual patient models. This order of registration (from representative model to the respective patient model) allows embodiments to track and map the trajectories of the SOI to patient models as illustrated in FIG. 2.

Figure 2:
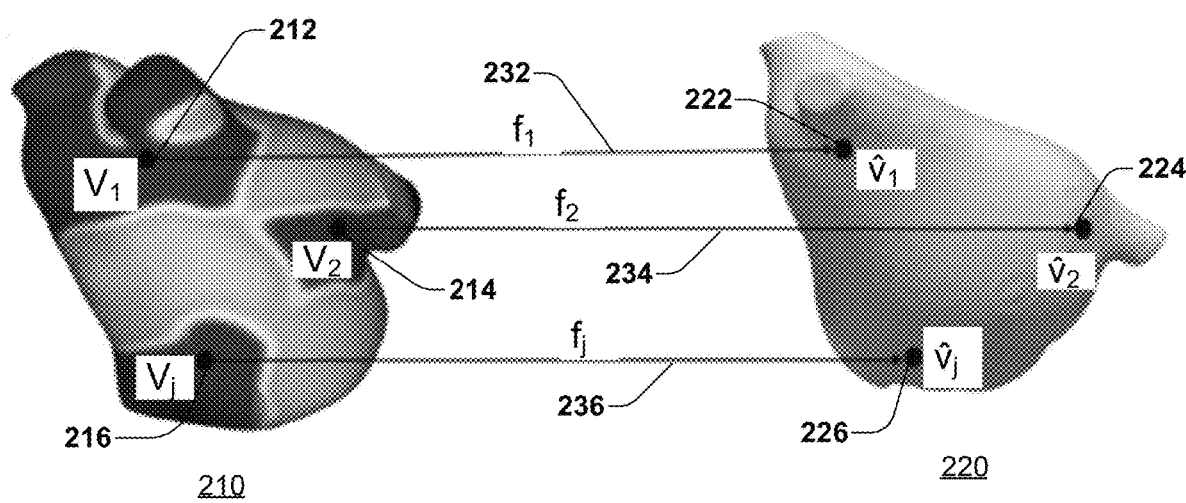
FIG. 2 illustrates transformation of a template atrial model to a patient atrial model according to embodiments described herein.

FIG. 2 illustrates a representative atrial model (e.g., template atlas) and patient atrial volume. The volume 210 illustrates the representative atrial model with indicated SOI regions 212-216 where there is significant shape difference between the two groups (AF+, AF−), with red areas indicating statistically significant difference with $p<0:05$. The set of vertices $S=\{v_j\}_1^N$ is the collection of nodes on the template surface in the region of sites of difference. A patient's left atrium 220 is also illustrated, and the corresponding image set is $\hat{S} = \{\hat{v}_j\}_1^N$.

Once the atlas has been aligned to the respective patient models, embodiments expressly extract the optimal displacement vectors $f_j$, illustrated at 232, 234, and 236, to create a feature map on the SOI based on the deformation field. The feature map comprises of the magnitude and curl of the deformation field. In particular, the norm of the deformation field (illustrated at 182) is equivalent to the amount of energy that is expended to distort template SOI to the patient SOI. The curl (illustrated at 184) represents the rotational acceleration that should be realized to transform the template SOI to a patient's SOI.

Embodiments compute an energy of the deformation field. The magnitude of the deformation on the SOI relates to the amount of force required to deform the atlas SOI to a patient's SOI. This feature is defined as:

$$d_j = \sqrt{\sum_{t \in \{x,y,z\}} (f_j^t)^2} \quad \text{Eq. 1}$$

where $f_j^t$ is the t-coordinate (x, y, or z, coordinate) of the displacement at node $v_j$ in S. For completeness we define the image of S to be $\hat{S}$. If the energy required to 'restore' the atlas SOI to the patient SOI is high, it manifests in a displacement field with large potential energy, which encodes high dissimilarity between the two bodies (i.e., SOIs).

Embodiments compute a curl of the deformation field, illustrated at 184. The curl of the displacement field at a node $v_j \in S$ is a vector denoted $c_j$, and is defined as $$c_j = \nabla \times f_j = \begin{vmatrix} i & j & k \\ \frac{\partial}{\partial x} & \frac{\partial}{\partial y} & \frac{\partial}{\partial z} \\ f_j^x & f_j^y & f_j^z \end{vmatrix} = \quad \text{Eq. 2}$$

$$\left(\frac{\partial f_j^z}{\partial y} - \frac{\partial f_j^y}{\partial z}\right)i + \left(\frac{\partial f_j^x}{\partial z} - \frac{\partial f_j^z}{\partial x}\right)j + \left(\frac{\partial f_j^y}{\partial x} - \frac{\partial f_j^x}{\partial y}\right)k$$

The curl of the deformation field on S defines the trajectories of the $v_j$'s towards $\hat{S}$. The curl of the deformation field quantifies the amount of micro rotations the SOI undergoes during registration to the patient model. If the magnitude of $c_j$ is zero (i.e. the components are all zero), the node $v_j$ does not undergo any rotation, whereas larger magnitudes of $c_j$ corresponds to double the angular speed of rotation. Since the curl and norm features are computed per node in S, embodiments compute statistics such as mean, maximum, minimum, and standard deviation for each patient.

Figure 6:
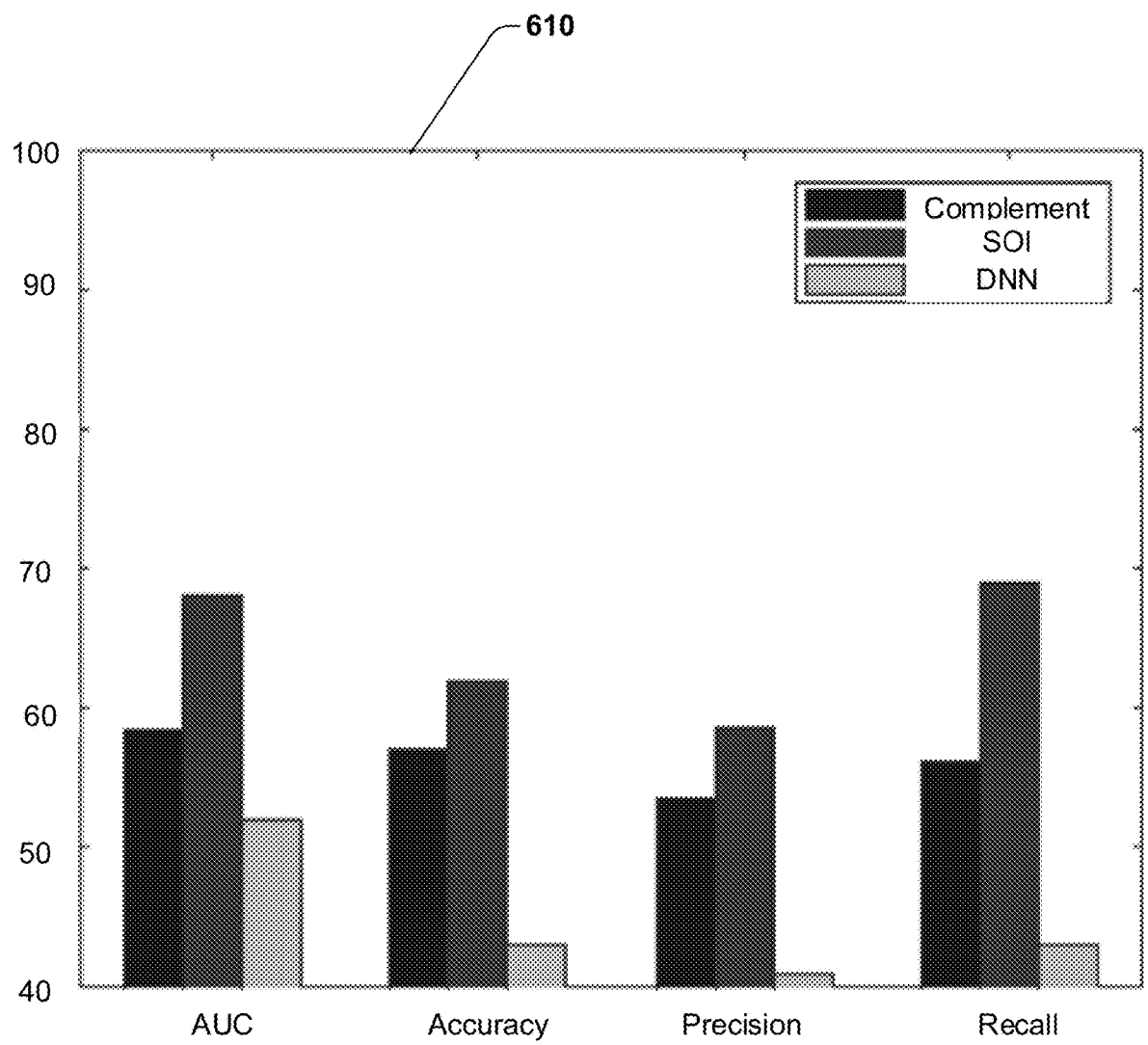
FIG. 6 illustrates bar charts comparing the performance of embodiments to other approaches.

In one embodiment, 30 atrial models (15 AF+ models, and 15 AF− models) are employed to estimate the SOI. Embodiments then extract features, illustrated at 154, for all the patients. In this example, the embodiment then performs one-hundred repeated runs of stratified 5-fold cross validation to assess the discriminability of the SOI feature maps. Embodiments employing the SOI features were also compared with features extracted from the complementary atrial sites, which indicates the superior discriminability of embodiments, which indicates that the SOI has more contribution to AF recurrence. Embodiments were compared with existing approaches that employ a deep learning based method for predicting recurrence from volumetric CT scans. FIG. 6 illustrates a bar chart 610 that compares the performance of embodiments employing SOI-derived features compared to the compliment site in four performance metrics: AUC, accuracy, precision, and recall. FIG. 6 further illustrates the comparative discriminability of embodiments vs. a 3D CNN classifier trained to distinguish AF+ from AF− patients.

The SOI as constructed by embodiments has higher discriminability power in predicting AF recurrence compared to the complimentary surface. Embodiments' performance was compared with the feature map on the complementary atrial SOI as well as with a Deep Learning architecture constructed for the study cohort. To demonstrate the contribution of the SOI in predicting AF recurrence, embodiments employing a Naive Bayes classifier model for the SOI features, and a Naïve Bayes classifier model for the complementary atrial surface features, were compared. Embodiments employing the SOI have better performance at predicting post-ablation AF recurrence than the remaining atrial surface.

Figure 3:
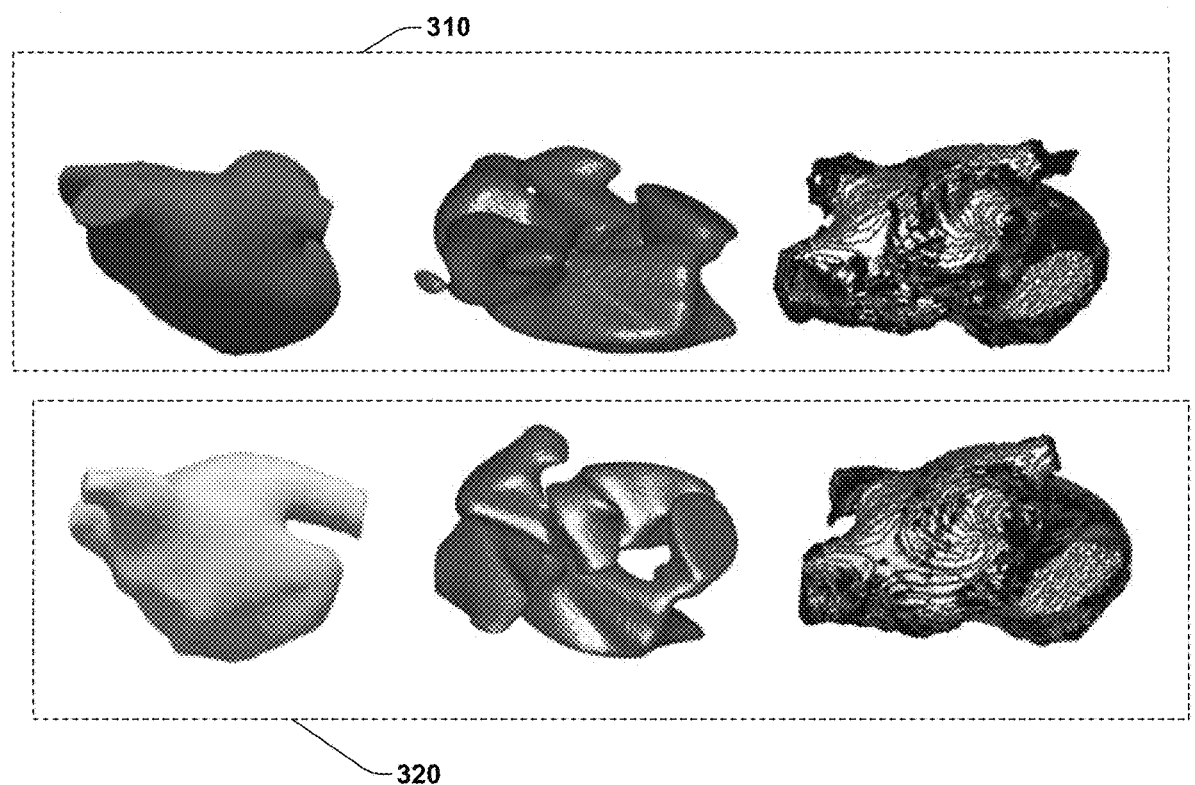
FIG. 3 illustrates features for an AF recurrent (AF+) patient and an AF non-recurrent (AF−) patient.
Figure 4:
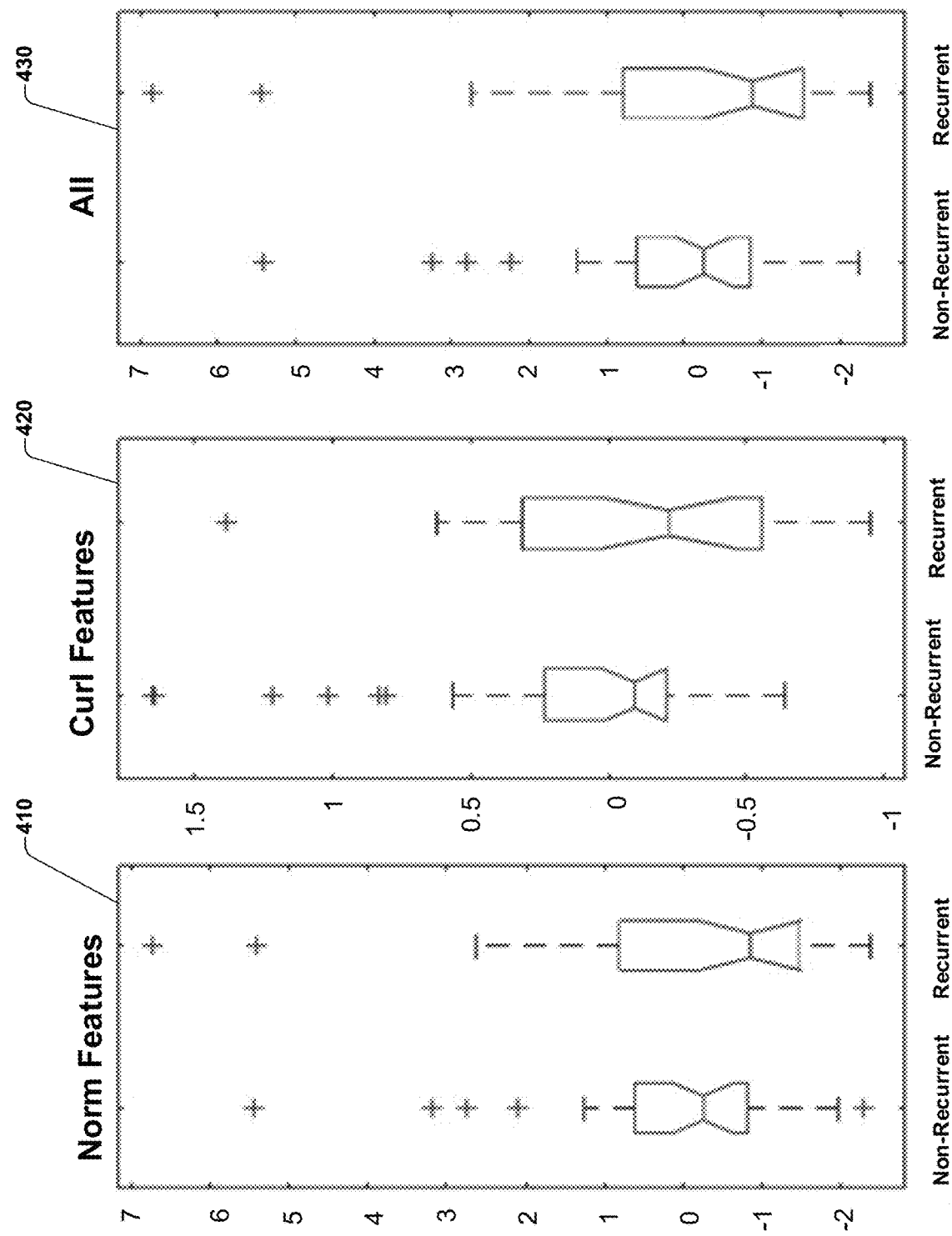
FIG. 4 illustrates box plots of features associated with AF+ and AF− patients.
Figure 5:
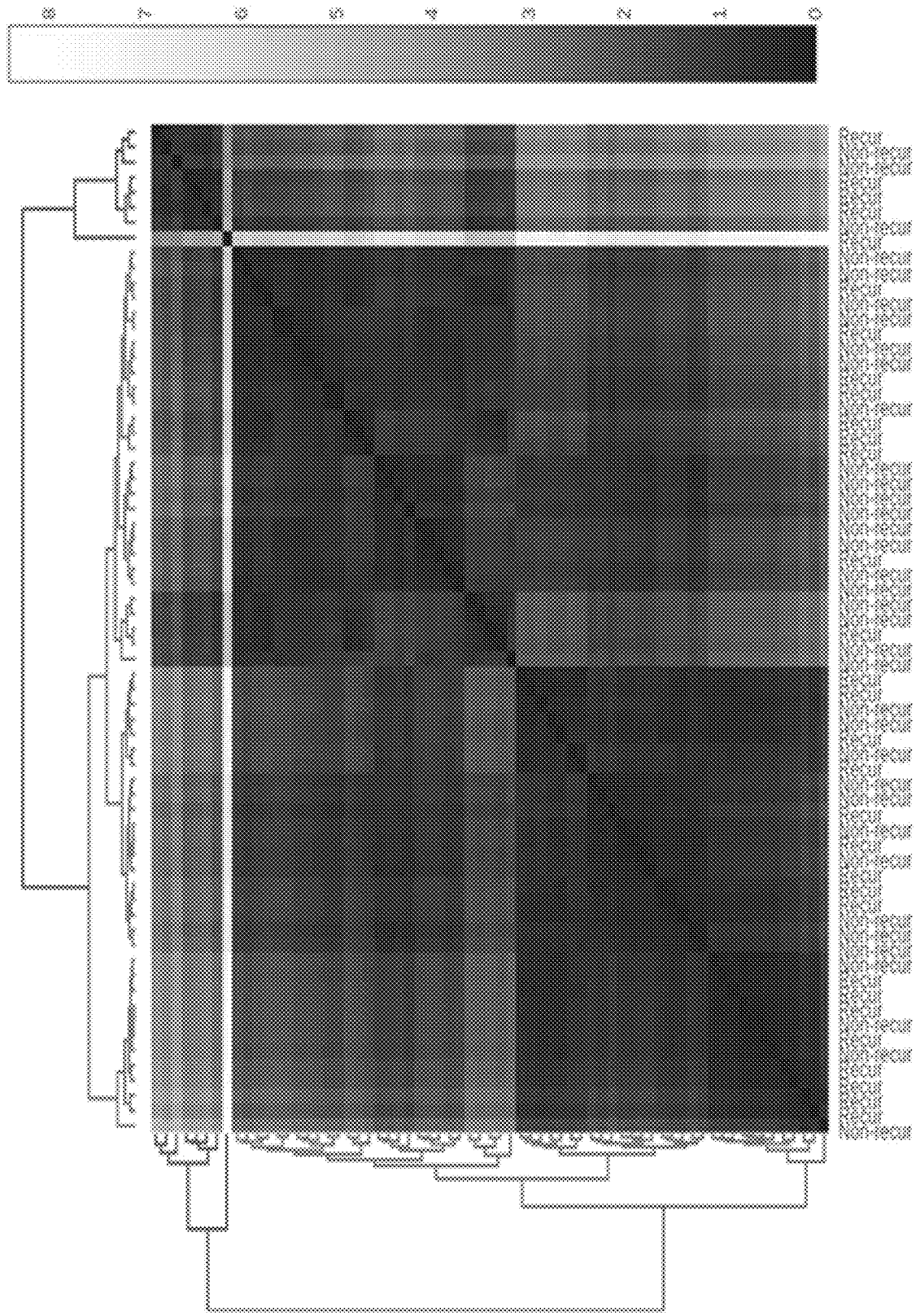
FIG. 5 illustrates consensus clustering according to embodiments.

The shape based features extracted with reference to the identified SOI may be evaluated against clinical parameters, through visualizations (with the aid of box and whisker plots, consensus clustering) and performance metrics of a naïve Bayes classifier. FIG. 3 illustrates features extracted by embodiments for an AF+ patient (i.e., recurrent) at 310, and for an AF− patient (i.e., late recurrence or non-recurrent) at 320. FIG. 4 illustrates box-whisker plots for norm features at 410, curl features at 420, and all features at 430. For the box-whisker plots, the dimensionality of both types of normalized features (e.g., norm, curl) was reduced using principal component analysis, keeping the first component for the box plots. Consensus clustering for the dataset is shown in FIG. 5. A classifier implemented according to embodiments using SOI-derived features outperforms a classifier employing the compliment site. Embodiments classify a patient as AF+ or AF− with an AUC of at least 0.67, which is a measurable improvement on existing approaches that employ clinical parameters (e.g., age and body mass index (BMI)), which distinguish AF+ from AF− patients with an AUC of only 0.63.

FIG. 7 illustrates an embodiment of a method 700 according to embodiments for computing a patient feature vector based on a patient model and a template model constructed from a differential atlas of atrial models. Method 700 is rendered in pseudo code.

Some portions of the detailed descriptions that follow are presented in terms of algorithms and symbolic representations of operations on data bits within a memory. These algorithmic descriptions and representations are used by those skilled in the art to convey the substance of their work to others. An algorithm, here and generally, is conceived to be a sequence of operations that produce a result. The operations may include physical manipulations of physical quantities. Usually, though not necessarily, the physical quantities take the form of electrical or magnetic signals capable of being stored, transferred, combined, compared, and otherwise manipulated in a logic, and so on. The physical manipulations create a concrete, tangible, useful, real-world result.

It has proven convenient at times, principally for reasons of common usage, to refer to these signals as bits, values, elements, symbols, characters, terms, numbers, and so on. It should be borne in mind, however, that these and similar terms are to be associated with the appropriate physical quantities and are merely convenient labels applied to these quantities. Unless specifically stated otherwise, it is appreciated that throughout the description, terms including processing, computing, calculating, determining, and so on, refer to actions and processes of a computer system, logic, processor, or similar electronic device that manipulates and transforms data represented as physical (electronic) quantities.

Example methods or operations may be better appreciated with reference to flow diagrams. While for purposes of simplicity of explanation, the illustrated methodologies are shown and described as a series of blocks, it is to be appreciated that the methodologies are not limited by the order of the blocks, as some blocks can occur in different orders and/or concurrently with other blocks from that shown and described. Moreover, less than all the illustrated blocks may be required to implement an example methodology. Blocks may be combined or separated into multiple components. Furthermore, additional and/or alternative methodologies can employ additional, not illustrated blocks.

Figure 8:
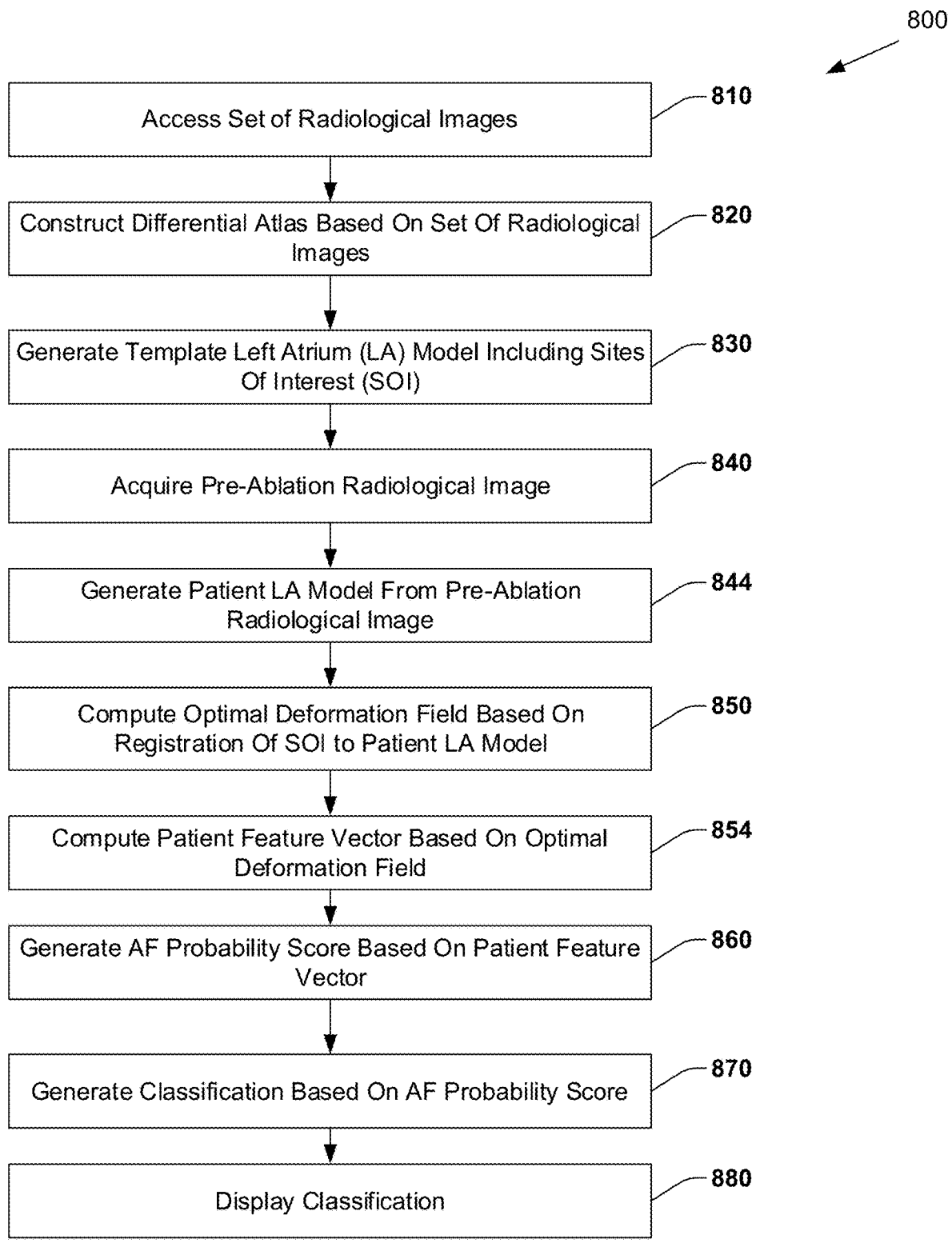
FIG. 8 illustrates example operations.

FIG. 8 illustrates a flow diagram of example operations 800 for predicting AF recurrence. In one embodiment, operations 800 includes identifying and characterizing differences induced by AF in a region of tissue demonstrating AF pathology. Operations 800 includes, at 810, accessing a set of radiological images acquired from a population of subjects, where a member of the set of radiological images includes a left atrium (LA) region. In one embodiment, the set of radiological images is acquired from a population of patients having experienced AF. The population includes an AF recurrence positive (AF+) subpopulation, and an AF recurrence negative (AF−) subpopulation. Each member of the set of radiological images includes an atrial mask that defines an LA represented in each member of the set of radiological images, respectively.

Figure 10:
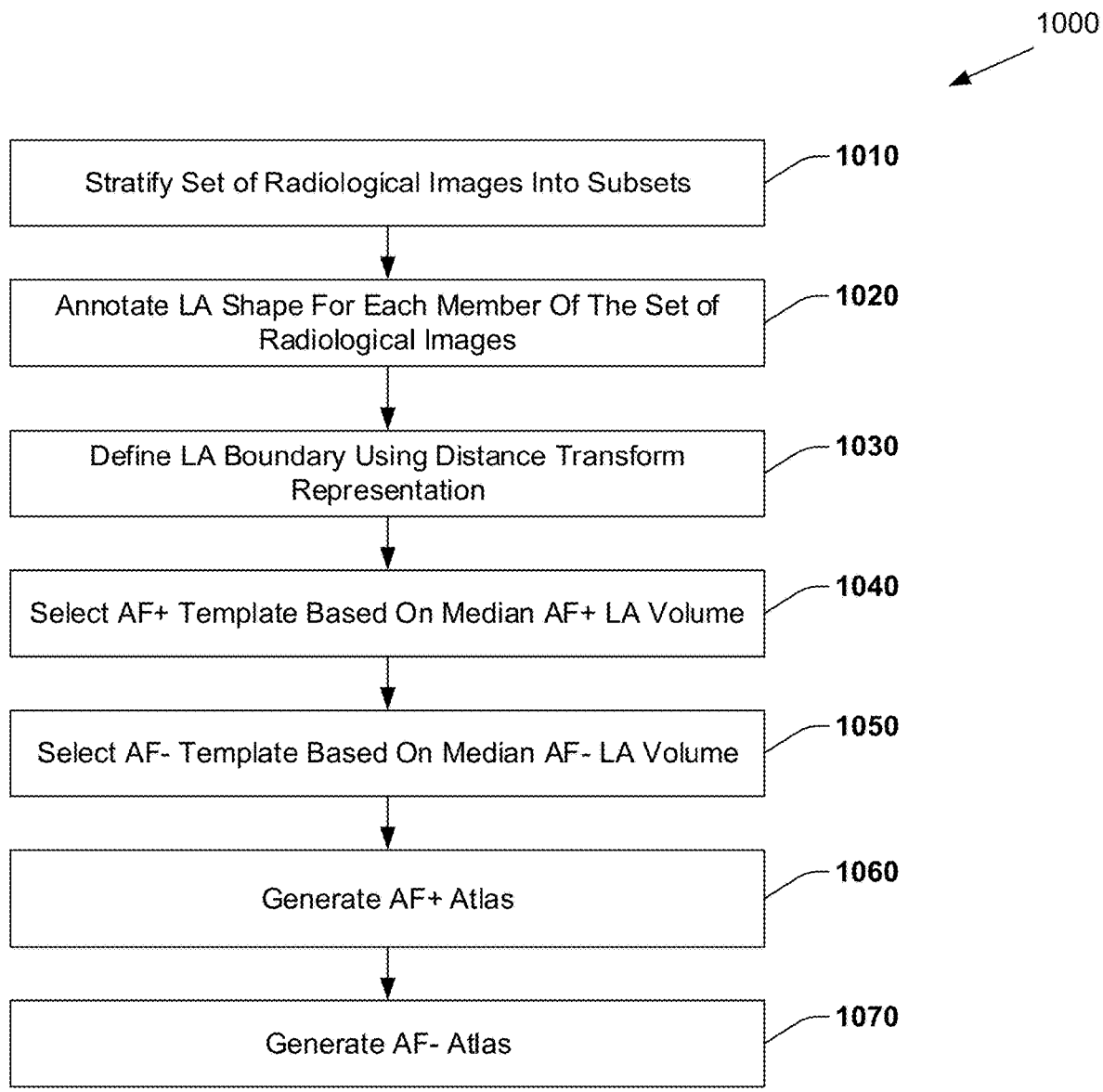
FIG. 10 illustrates example operations.

Operations 800 also includes, at 820, constructing a statistical shape differential atlas from the set of radiological images. FIG. 10 illustrates example operations 1000 for constructing a statistical shape differential atlas. Operations 1000 includes, at 1010 stratifying the set of radiological images into a subset of radiological images associated with a subpopulation of subjects, where a subject belongs to the AF+ subpopulation, or the AF− subpopulation.

Operations 1000 also includes, at 1020, annotating an LA shape for each member of the set of radiological images, respectively. In one embodiment, the LA shape is annotated using an automated annotation technique.

Operations 1000 also includes, at 1030, defining an LA boundary by transforming the LA shape into a distance transform representation, where the LA boundary defines a volume for the LA shape.

Operations 1000 also includes, at 1040, selecting an AF+ template by selecting the member of the AF+ subpopulation having the median volume for the AF+ subpopulation.

Operations 1000 also includes, at 1050, selecting an AF− template by selecting the member of the AF− subpopulation having the median volume for the AF− subpopulation.

Operations 1000 also includes, at 1060, generating an AF+ atlas by registering each member of the AF+ subpopulation to the AF+ template. In one embodiment, generating the AF+ atlas by registering each member of the AF+ subpopulation to the AF+ template comprises: a first registration of each member of the AF+ subpopulation to the AF+ template using an affine registration, where the transformation parameters of the affine registration are determined using a block matching strategy; and a second registration of each member of the AF+ subpopulation to the AF+ template using a B-spline based non-rigid registration. In one embodiment, less than each member of the AF+ subpopulation may be registered.

Operations 1000 also includes, at 1070, generating an AF− atlas by registering each member of the AF− subpopulation to the AF− template. In one embodiment, generating the AF− atlas by registering each member of the AF− subpopulation to the AF− template comprises: a first registration of each member of the AF− subpopulation to the AF− template using an affine registration, where the transformation parameters of the affine registration are determined using a block matching strategy; and a second registration of each member of the AF− subpopulation to the AF− template using a B-spline based non-rigid registration. In one embodiment, less than each member of the AF− subpopulation may be registered.

Returning to FIG. 8, operations 800 also includes, at 830, generating a template LA model from the statistical shape differential atlas. The template LA model includes a site of interest (SOI).

Operations 800 also includes, at 840, acquiring a pre-ablation radiological image of a region of tissue in a patient demonstrating atrial fibrillation (AF) pathology. In one embodiment, the pre-ablation radiological image is a CE-CTA image. In one embodiment, a set of clinical parameters associated with the patient are also acquired. Clinical parameters may include, for example, left atrial volume (LAV), left ventricular ejection fraction (LVEF), body mass index (BMI), sinus rhythm at the time of ablation, and AF type (paroxysmal vs. persistent).

Operations 800 also includes, at 844, generating a patient LA model from the pre-ablation radiological image. In one embodiment, generating the template LA model from the statistical shape differential atlas, where the template LA model includes a site of interest (SOI) comprises: registering the atrial mask of each member of the AF+ subpopulation to the AF− atlas; identifying a statistically significant shape difference between the AF+ subpopulation and the AF− subpopulation based on the registration of the atrial mask of each member of the AF+ subpopulation to the AF− atlas; and defining the SOI based on the statistically significant shape difference. In one embodiment, the statistically significant shape difference is identified using a general linear model (GLM) based t-test framework.

Operations 800 also includes, at 850, computing an optimal deformation field that registers the SOI to the patient LA model using a deformable registration approach.

Figure 9:
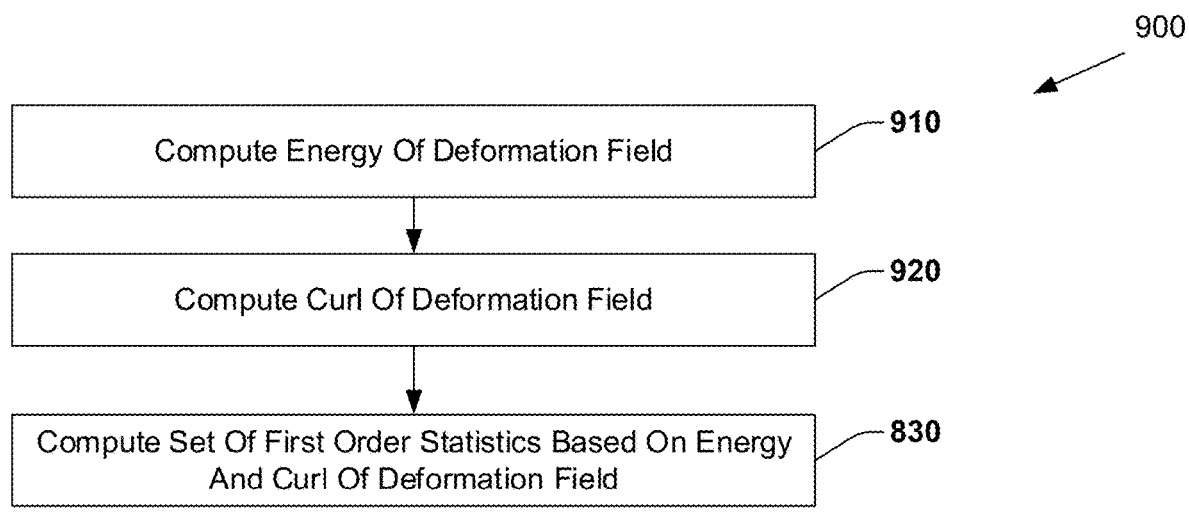
FIG. 9 illustrates example operations.

Operations 800 also includes, at 854, computing a patient feature vector based on the optimal deformation field. FIG. 9 is a flow diagram of operations 900 for computing a patient feature vector field. In one embodiment, computing the patient feature vector includes, at 910, computing an energy of the deformation field. Computing the patient feature vector also includes, at 920, computing a curl of the deformation field. Computing the patient feature vector further includes, at 930, computing a set of first-order statistics based on the energy of the deformation field and the curl of the deformation field. In one embodiment, the set of first-order statistics includes: a minimum of the energy, a mean of the energy, a maximum of the energy, or a standard deviation of the energy, and a minimum of the curl, a mean of the curl, a maximum of the curl, or a standard deviation of the curl. The set of first order statistics based on the energy of the deformation field and the curl of the deformation field may be computed across the mesh points of the SOI.

Operations 800 also includes, at 860, generating an AF probability score for the patient based, at least in part, on the patient feature vector. The AF probability score may represent the probability that the patient associated with the radiological image will develop AF recurrence within a period of time. In one embodiment, generating the AF probability score for the patient based, at least in part, on the patient feature vector comprises: providing the patient feature vector to a naïve Bayes classifier configured to distinguish a patient who will experience AF recurrence from a patient who will not experience AF recurrence; and receiving, from the naïve Bayes classifier, a probability that the patient will experience AF recurrence. In another embodiment, generating the AF probability score for the patient based, at least in part, on the patient feature vector may include providing the patient feature vector to a machine learning classifier, including a quadratic discriminant analysis (QDA) classifier, a linear discriminant analysis (LDA) classifier, a random forest classifier, or a support vector machine.

Operations 800 also includes, at 870, generating a classification of the patient based, at least in part, on the AF probability score. In one embodiment, generating the classification includes classifying the region of tissue as AF+ or AF−. Embodiments may generate a classification of the patient associated with the radiological image. Embodiments may classify the patient as likely to develop AF recurrence within a period of time, or unlikely to develop AF recurrence within the period of time. In one embodiment, the classification may be further based on the set of clinical parameters.

Operations 800 further include, at 880, displaying the classification or the AF probability score. Displaying the classification or the AF probability score may include displaying the classification or the AF probability score on a computer monitor, a smartphone display, a tablet display, or other displays. Displaying the classification or the AF probability score may also include printing the classification or the AF probability score. Displaying the classification or the AF probability score may also include controlling an AF recurrence prediction system, an atrial classification system, a personalized medicine system, a computer assisted diagnostic ($CAD_x$), system a monitor, or other display, to display operating parameters or characteristics of a machine learning classifier, including a naïve Bayes classifier, during both training and testing, or during clinical operation of the machine learning classifier. By displaying the classification or the AF probability score, example embodiments provide a timely and intuitive way for a human medical practitioner to more accurately predict AF recurrence in AF patients.

Example methods and apparatus facilitate applying a more appropriately determined treatment based on the patient feature vector or the classification. Using a more appropriately determined and applied treatment may lead to less therapeutics being required for a patient or may lead to avoiding or delaying a biopsy, a resection, or other invasive procedure. When regions of tissue, including the LA detected in CT images, including CE-CTA imagers, or the patient associated with the region of tissue, are more quickly and more accurately classified as likely or unlikely to experience post-ablation AF recurrence, patients with poorer prognoses may receive a higher proportion of scarce resources (e.g., therapeutics, physician time and attention, hospital beds) while those with better prognoses may be spared unnecessary treatment, which in turn spares unnecessary expenditures and resource consumption. Example methods and apparatus may thus have the real-world, quantifiable effects of improving patient outcomes and reducing resource expenditure.

While FIGS. 8, 9, and 10 illustrate various actions occurring in serial, it is to be appreciated that various actions illustrated in FIG. 8, 9, or 10 could occur substantially in parallel. By way of illustration, a first process could access a set of CT images from a population of patients, a second process could construct a statistical shape atlas, and a third process could generate a patient feature vector. While three processes are described, it is to be appreciated that a greater or lesser number of processes could be employed and that lightweight processes, regular processes, threads, and other approaches could be employed. The operations 800, 900, and 1000 include acquiring electronic data, reading from a computer file, receiving a computer file, reading from a computer memory, or other computerized activity not practically performed in a human mind.

In one example, operations or a method may be implemented as computer executable instructions. Thus, in one example, a computer-readable storage medium may store computer executable instructions that if executed by a machine (e.g., computer) cause the machine to perform methods or operations described or claimed herein including operations 800, 900, or 1000. While executable instructions associated with the listed operations are described as being stored on a computer-readable storage medium, it is to be appreciated that executable instructions associated with other example methods described or claimed herein may also be stored on a computer-readable storage medium. In different embodiments, the example methods described herein may be triggered in different ways. In one embodiment, a method or operation may be triggered manually by a user. In another example, a method or operation may be triggered automatically.

Figure 11:
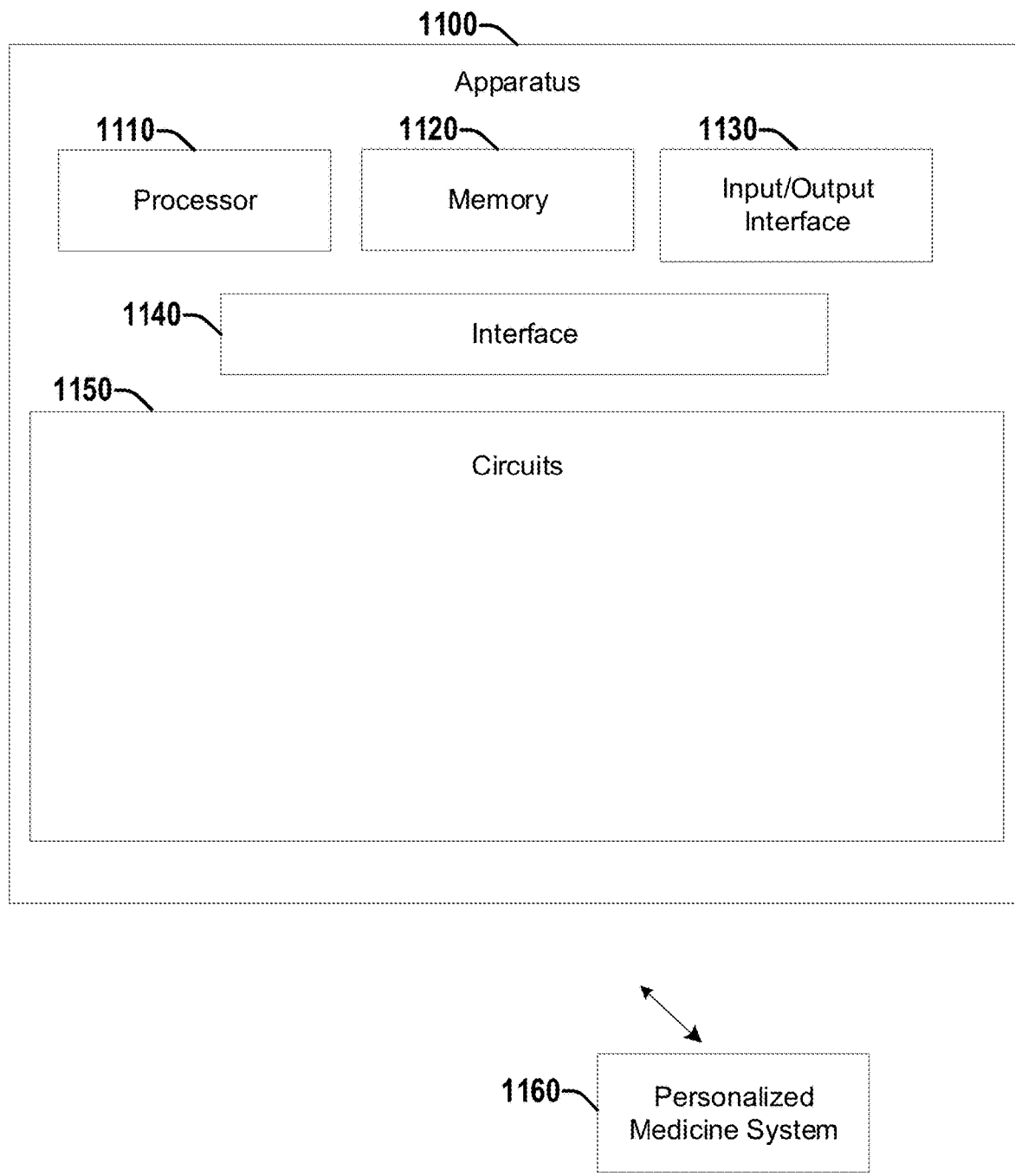
FIG. 11 illustrates an example apparatus according to embodiments described herein.

FIG. 11 illustrates an example apparatus 1100 for predicting AF recurrence in a region of tissue demonstrating AF pathology in an image. Apparatus 1100 may be configured to generate a patient feature vector, generate an AF probability score based on the patient feature vector, and classify a region of tissue or a patient into a positive class or a negative class (e.g., AF+, AF−) based on the AF probability score. Apparatus 1100 includes a processor 1110. Apparatus 1100 also includes a memory 1120. Processor 1110 may, in one embodiment, include circuitry such as, but not limited to, one or more single-core or multi-core processors. Processor 1110 may include any combination of general-purpose processors and dedicated processors (e.g., graphics processors, application processors, etc.). The processors may be coupled with or may include memory (e.g. memory 1120) or storage and may be configured to execute instructions stored in the memory 1120 or storage to enable various apparatus, applications, or operating systems to perform the operations.

Memory 1120 is configured to store a digitized image of a region of interest demonstrating AF pathology. Memory 1120 may be configured to store a set of computed tomography (CT) images acquired from a population of subjects, where a member of the set of CT images includes a left atrium (LA) region, where the set of CT images is acquired from a population of patients, where the population includes an atrial fibrillation (AF) recurrence positive (AF+) subpopulation, and an AF recurrence negative (AF−) subpopulation; where each member of the set of CT images includes an atrial mask that defines an LA represented in each member of the set of CT images, respectively. A member of the set of CT images may be, in one embodiment, a CE-CTA image. Memory 1120 may be further configured to store other types of medical imagery, including, for example, MRI imagery.

Memory 1120 may be further configured to store a first training set of images demonstrating AF pathology, or a first testing set of images demonstrating AF pathology. At least one member of the first training set is classified as likely to experience AF recurrence, and at least one other, different member of the first training set is classified as unlikely to experience AF recurrence. At least one member of the first testing set is classified as likely to experience AF recurrence, and at least one other, different member of the first testing set is classified as unlikely to experience AF recurrence. In another embodiment, a training set or a testing set may include radiological imagery of other, different positive and negative classes.

Apparatus 1100 also includes an input/output (I/O) interface 1130, a set of circuits 1150, and an interface 1140 that connects the processor 1110, the memory 1120, the I/O interface 1130, and the set of circuits 1150. I/O interface 1130 may be configured to transfer data between memory 1120, processor 1110, circuits 1150, and external devices, for example, an AF recurrence prediction system, an atrial classification system, a $CAD_x$ system, an MRI system, a CT system, or other medical imaging system. Circuits 1150 or processor 1110 may be configured to perform operations or methods described herein, including but not limited to operations 800, 900, or 1000.

Apparatus 1100 may also include a personalized medicine system 1160. Personalized medicine system 1160, or other embodiments described herein, may be configured to generate a personalized AF treatment plan based on the classification, the AF probability score, or the patient feature vector. For example, for a region of tissue demonstrating AF classified as likely to experience post-ablation AF recurrence, a first treatment plan may be generated, while for a region of tissue classified as unlikely to experience post-ablation AF recurrence, a second, different treatment plan may be generated. Different personalized treatment plans may also generate different follow-up or monitoring schedules depending on the classification. For example, a patient classified as AF+ may, according to the personalized cancer treatment plan, be subjected to more frequent monitoring, than a patient classified as AF−.

Figure 12:
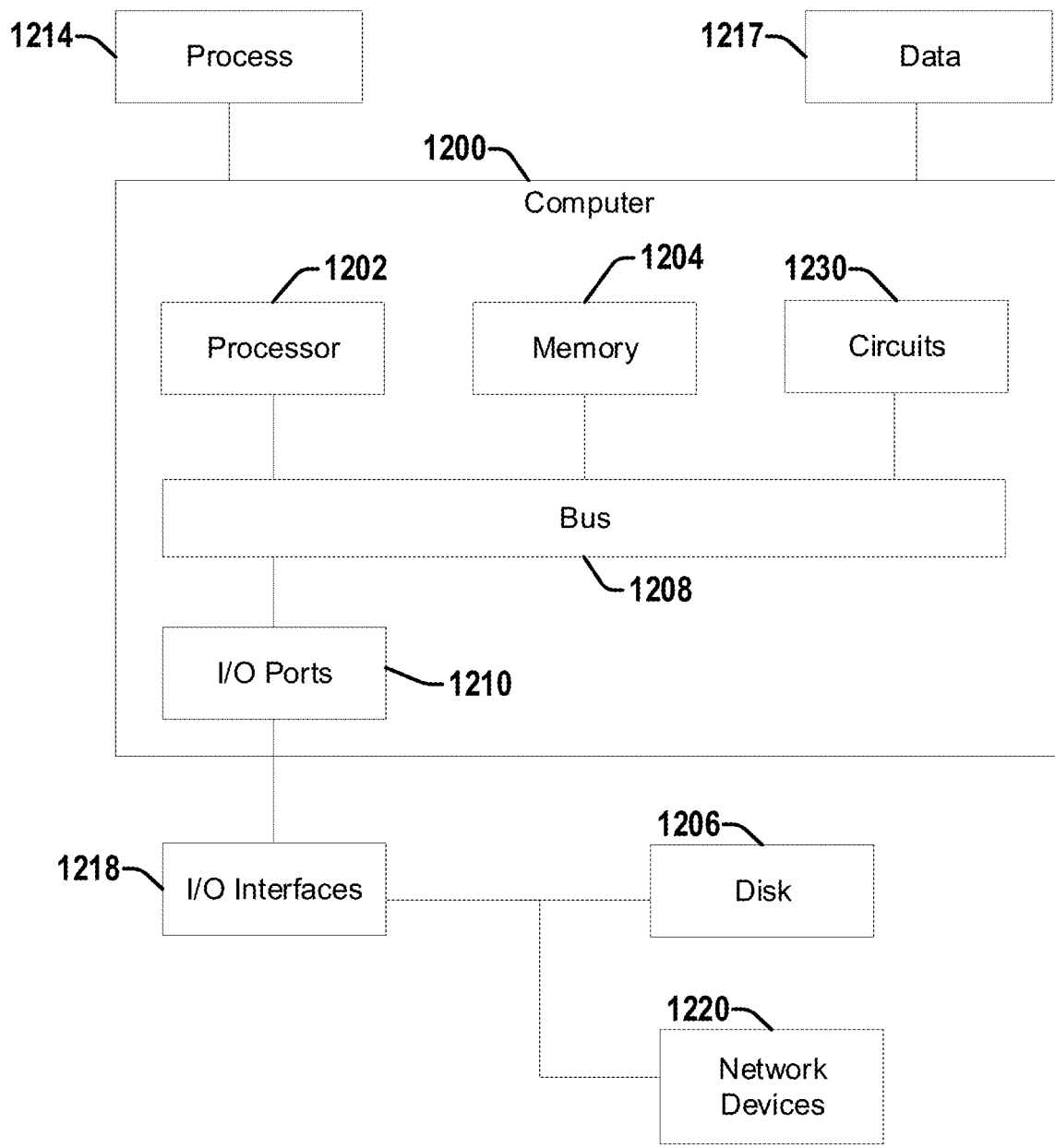
FIG. 12 an example computer in which example operations and methods described herein operate.

FIG. 12 illustrates an example computer 1200 in which example methods illustrated herein can operate and in which example methods, apparatus, circuits, operations, or logics may be implemented. In different examples, computer 1200 may be part of an AF recurrence prediction system or apparatus, a $CAD_x$ system, an MRI system, a CT system, a digital whole slide scanner, or a personalized medicine system, or may be operably connectable to an AF recurrence prediction system or apparatus, a $CAD_x$ system, an MRI system, a CT system, a digital whole slide scanner, or a personalized medicine system.

Computer 1200 includes a processor 1202, a memory 1204, and input/output (I/O) ports 1210 operably connected by a bus 1208. In one example, computer 1200 may include a set of logics or circuits 1230 that perform operations for or a method of predicting AF recurrence in radiological imagery, including by using a machine learning classifier. Thus, the set of circuits 1230, whether implemented in computer 1200 as hardware, firmware, software, and/or a combination thereof may provide means (e.g., hardware, firmware, circuits) for predicting AF recurrence in radiological imagery. In different examples, the set of circuits 1230 may be permanently and/or removably attached to computer 1200.

Processor 1202 can be a variety of various processors including dual microprocessor and other multi-processor architectures. Processor 1202 may be configured to perform steps of methods claimed and described herein. Memory 1204 can include volatile memory and/or non-volatile memory. A disk 1206 may be operably connected to computer 1200 via, for example, an input/output interface (e.g., card, device) 1218 and an input/output port 1210. Disk 1206 may include, but is not limited to, devices like a magnetic disk drive, a tape drive, a Zip drive, a flash memory card, or a memory stick. Furthermore, disk 1206 may include optical drives like a CD-ROM or a digital video ROM drive (DVD ROM). Memory 1204 can store processes 1214 or data 1217, for example. Data 1217 may, in one embodiment, include digitized radiological images, including CT images of heart tissue. Disk 1206 or memory 1204 can store an operating system that controls and allocates resources of computer 1200.

Bus 1208 can be a single internal bus interconnect architecture or other bus or mesh architectures. While a single bus is illustrated, it is to be appreciated that computer 1200 may communicate with various devices, circuits, logics, and peripherals using other buses that are not illustrated (e.g., PCIE, SATA, Infiniband, 1394, USB, Ethernet).

Computer 1200 may interact with input/output devices via I/O interfaces 1218 and input/output ports 1210. Input/output devices can include, but are not limited to, CT systems, MRI systems, digital whole slide scanners, an optical microscope, a keyboard, a microphone, a pointing and selection device, cameras, video cards, displays, disk 1206, network devices 1220, or other devices. Input/output ports 1210 can include but are not limited to, serial ports, parallel ports, or USB ports.

Computer 1200 may operate in a network environment and thus may be connected to network devices 1220 via I/O interfaces 1218 or I/O ports 1210. Through the network devices 1220, computer 1200 may interact with a network. Through the network, computer 1200 may be logically connected to remote computers. The networks with which computer 1200 may interact include, but are not limited to, a local area network (LAN), a wide area network (WAN), or other networks, including the cloud.

Example 1 is non-transitory computer-readable storage device storing instructions that when executed by a processor control the processor to perform operations, the operations comprising: accessing a set of radiological images acquired from a population of subjects, where a member of the set of radiological images includes a left atrium (LA) region; constructing a statistical shape differential atlas from the set of radiological images; generating a template LA model from the statistical shape differential atlas, where the template LA model includes a site of interest (SOI); acquiring a pre-ablation radiological image of a region of tissue in a patient demonstrating atrial fibrillation (AF) pathology; generating a patient LA model from the pre-ablation radiological image; computing an optimal deformation field that registers the SOI to the patient LA model using a deformable registration approach; computing a patient feature vector based on the optimal deformation field; generating an AF probability score for the patient based, at least in part, on the patient feature vector; generating a classification of the patient based, at least in part, on the AF probability score; and displaying the classification or the AF probability score.

Example 2 comprises the subject matter of any variation of any of example(s) 1, where computing the patient feature vector comprises: computing an energy of the deformation field; computing a curl of the deformation field; and computing a set of first-order statistics based on the energy of the deformation field and the curl of the deformation field.

Example 3 comprises the subject matter of any variation of any of example(s) 1-2, where the set of first-order statistics based on the energy of the deformation field and the curl of the deformation field includes: a minimum of the energy, a mean of the energy, a maximum of the energy, or a standard deviation of the energy, and a minimum of the curl, a mean of the curl, a maximum of the curl, or a standard deviation of the curl.

Example 4 comprises the subject matter of any variation of any of example(s) 1-3 where the set of radiological images is acquired from a population of patients, where the population includes an AF recurrence positive (AF+) subpopulation, and an AF recurrence negative (AF−) subpopulation; where each member of the set of radiological images includes an atrial mask that defines an LA represented in each member of the set of radiological images, respectively.

Example 5 comprises the subject matter of any variation of any of example(s) 1-4 where constructing the statistical shape differential atlas comprises: stratifying the set of radiological images into a subset of radiological images associated with a subpopulation of subjects, where a subject belongs to the AF+ subpopulation, or the AF− subpopulation; annotating an LA shape for each member of the set of radiological images, respectively; defining an LA boundary by transforming the LA shape into a distance transform representation, where the LA boundary defines a volume for the LA shape; selecting an AF+ template by selecting the member of the AF+ subpopulation having the median volume for the AF+ subpopulation; selecting an AF− template by selecting the member of the AF− subpopulation having the median volume for the AF− subpopulation; generating an AF+ atlas by registering each member of the AF+ subpopulation to the AF+ template; and generating an AF− atlas by registering each member of the AF− subpopulation to the AF− template.

Example 6 comprises the subject matter of any variation of any of example(s) 1-5, where generating the AF+ atlas by registering each member of the AF+ subpopulation to the AF+ template comprises: a first registration of each member of the AF+ subpopulation to the AF+ template using an affine registration, where the transformation parameters of the affine registration are determined using a block matching strategy; and a second registration of each member of the AF+ subpopulation to the AF+ template using a B-spline based non-rigid registration.

Example 7 comprises the subject matter of any variation of any of example(s) 1-6, where generating the AF− atlas by registering each member of the AF− subpopulation to the AF− template comprises: a first registration of each member of the AF− subpopulation to the AF− template using an affine registration, where the transformation parameters of the affine registration are determined using a block matching strategy; and a second registration of each member of the AF− subpopulation to the AF− template using a B-spline based non-rigid registration.

Example 8 comprises the subject matter of any variation of any of example(s) 1-7, where generating the template LA model from the statistical shape differential atlas, where the template LA model includes a site of interest (SOI) comprises: registering the atrial mask of each member of the AF+ subpopulation to the AF− atlas; identifying a statistically significant shape difference between the AF+ subpopulation and the AF− subpopulation based on the registration of the atrial mask of each member of the AF+ subpopulation to the AF− atlas; and defining the SOI based on the statistically significant shape difference.

Example 9 comprises the subject matter of any variation of any of example(s) 1-8, where the statistically significant shape difference is identified using a general linear model (GLM) based t-test framework.

Example 10 comprises the subject matter of any variation of any of example(s) 1-9, where a member of the set of radiological images or the pre-ablation radiological image is a non-contrast computed tomography (CT) image or a contrast-enhanced computed tomography angiography (CE-CTA) image Example 11 comprises the subject matter of any variation of any of example(s) 1-10, where a member of the set of radiological images or the pre-ablation radiological image is a magnetic resonance imaging (MRI) image.

Example 12 comprises the subject matter of any variation of any of example(s) 1-11, where generating the AF probability score for the patient based, at least in part, on the patient feature vector comprises: providing the patient feature vector to a naïve Bayes classifier configured to distinguish a patient who will experience AF recurrence from a patient who will not experience AF recurrence; and receiving, from the naïve Bayes classifier, a probability that the patient will experience AF recurrence.

Example 13 comprises apparatus comprising: a memory configured to store a set of computed tomography (CT) images acquired from a population of subjects, where a member of the set of CT images includes a left atrium (LA) region, where the set of CT images is acquired from a population of patients, where the population includes an atrial fibrillation (AF) recurrence positive (AF+) subpopulation, and an AF recurrence negative (AF−) subpopulation; where each member of the set of CT images includes an atrial mask that defines an LA represented in each member of the set of CT images, respectively; and one or more processors configured to: access the set of CT images; construct a statistical shape differential atlas from the set of CT images; generate a template LA model from the statistical shape differential atlas, where the template LA model includes a site of interest (SOI); acquire a pre-ablation CT image of a region of tissue in a patient demonstrating AF pathology; generate a patient LA model from the pre-ablation CT image; compute an optimal deformation field that registers the SOI to the patient LA model using a deformable registration approach; compute a patient feature vector based on the optimal deformation field; generate an AF probability score for the patient based, at least in part, on the patient feature vector; generate a classification of the patient demonstrating AF pathology based, at least in part, on the AF probability score; and display the classification or the AF probability score.

Example 14 comprises the subject matter of any variation of any of example(s) 13, where computing the patient feature vector comprises: computing an energy of the deformation field; computing a curl of the deformation field; and computing a set of first-order statistics based on the energy of the deformation field and the curl of the deformation field.

Example 15 comprises the subject matter of any variation of any of example(s) 13-14, where constructing the statistical shape differential atlas comprises: stratifying the set of radiological images into a subset of radiological images associated with a subpopulation of subjects, where a subject belongs to the AF+ subpopulation, or the AF− subpopulation; annotating an LA shape for each member of the set of radiological images, respectively; defining an LA boundary by transforming the LA shape into a distance transform representation, where the LA boundary defines a volume for the LA shape; selecting an AF+ template by selecting the member of the AF+ subpopulation having the median volume for the AF+ subpopulation; selecting an AF− template by selecting the member of the AF− subpopulation having the median volume for the AF− subpopulation; generating an AF+ atlas by registering each member of the AF+ subpopulation to the AF+ template; and generating an AF− atlas by registering each member of the AF− subpopulation to the AF− template.

Example 16 comprises the subject matter of any variation of any of example(s) 13-15, where generating the AF+ atlas by registering each member of the AF+ subpopulation to the AF+ template comprises: a first registration of each member of the AF+ subpopulation to the AF+ template using an affine registration, where the transformation parameters of the affine registration are determined using a block matching strategy; and a second registration of each member of the AF+ subpopulation to the AF+ template using a B-spline based non-rigid registration.

Example 17 comprises the subject matter of any variation of any of example(s) 13-16, where generating the AF− atlas by registering each member of the AF− subpopulation to the AF− template comprises: a first registration of each member of the AF− subpopulation to the AF− template using an affine registration, where the transformation parameters of the affine registration are determined using a block matching strategy; and a second registration of each member of the AF− subpopulation to the AF− template using a B-spline based non-rigid registration.

Example 18 comprises the subject matter of any variation of any of example(s) 13-17, where generating the template LA model from the statistical shape differential atlas, where the template LA model includes a site of interest (SOI) comprises: registering the atrial mask of each member of the AF+ subpopulation to the AF− atlas; identifying a statistically significant shape difference between the AF+ subpopulation and the AF− subpopulation based on the registration of the atrial mask of each member of the AF+ subpopulation to the AF− atlas using a general linear model (GLM) based t-test framework; and defining the SOI based on the statistically significant shape difference.

Example 19 comprises the subject matter of any variation of any of example(s) 13-18, where generating the AF probability score for the patient based, at least in part, on the patient feature vector comprises: providing the patient feature vector to a naïve Bayes classifier configured to distinguish a patient who will experience AF recurrence from a patient who will not experience AF recurrence; and receiving, from the naïve Bayes classifier, a probability that the patient will experience AF recurrence.

Example 20 comprises non-transitory computer-readable storage device storing executable instructions that, in response to execution, cause an atrial fibrillation (AF) recurrence prediction device to perform operations for producing a quantification of differences between a pre-ablation image of a left atrium (LA) and a statistical shape atlas, the operations comprising: accessing a set of computed tomography (CT) images acquired from a population of subjects, where a member of the set of CT images includes a left atrium (LA) region; constructing a statistical shape differential atlas from the set of CT images; generating a template LA model from the statistical shape differential atlas, where the template LA model includes a site of interest (SOI); acquiring a pre-ablation CT image of a region of tissue in a patient demonstrating AF pathology; generating a patient LA model from the pre-ablation CT image; computing an optimal deformation field that registers the SOI to the patient LA model using a deformable registration approach; computing a patient feature vector based on the optimal deformation field; generating an AF probability score for the patient based, at least in part, on the patient feature vector; generating a classification of the patient based, at least in part, on the AF probability score; generating a personalized AF treatment plan based on the classification, the AF probability score, and the pre-ablation CT image; and displaying the personalized AF treatment plan, the classification, the AF probability score, or the pre-ablation CT image.

Example 21 comprises an apparatus comprising means for executing any of the described operations of examples 1-20.

Example 22 comprises a machine readable medium that stores instructions for execution by a processor to perform any of the described operations of examples 1-20.

Example 23 comprises an apparatus comprising: a memory interface; and processing circuitry (e.g., circuits 1150, circuits 1230) configured to: perform any of the described operations of examples 1-20.

While the operations or methods described herein are illustrated and described above as a series of acts or events, it will be appreciated that the illustrated ordering of such acts or events are not to be interpreted in a limiting sense. For example, some acts may occur in different orders and/or concurrently with other acts or events apart from those illustrated and/or described herein. In addition, not all illustrated acts may be required to implement one or more aspects or embodiments of the disclosure herein. Also, one or more of the acts depicted herein may be carried out in one or more separate acts and/or phases.

While apparatus have been illustrated and described with respect to one or more implementations, alterations and/or modifications may be made to the illustrated examples without departing from the spirit and scope of the appended claims. In particular regard to the various functions performed by the above described components or structures (assemblies, devices, circuits, systems, etc.), the terms (including a reference to a "means") used to describe such components are intended to correspond, unless otherwise indicated, to any component or structure which performs the specified function of the described component (e.g., that is functionally equivalent), even though not structurally equivalent to the disclosed structure which performs the function in the herein illustrated exemplary implementations of the invention.

In particular regard to the various functions performed by the above described components (assemblies, devices, circuits, systems, etc.), the terms (including a reference to a "means") used to describe such components are intended to correspond, unless otherwise indicated, to any component or structure which performs the specified function of the described component (e.g., that is functionally equivalent), even though not structurally equivalent to the disclosed structure which performs the function in the herein illustrated exemplary implementations of the disclosure. In addition, while a particular feature may have been disclosed with respect to only one of several implementations, such feature may be combined with one or more other features of the other implementations as may be desired and advantageous for any given or particular application.

References to "one embodiment", "an embodiment", "one example", and "an example" indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

"Computer-readable storage medium", as used herein, refers to a medium that stores instructions or data. "Computer-readable storage medium" does not refer to propagated signals. A computer-readable storage medium may take forms, including, but not limited to, non-volatile media, and volatile media. Non-volatile media may include, for example, optical disks, magnetic disks, tapes, and other media. Volatile media may include, for example, semiconductor memories, dynamic memory, and other media. Common forms of a computer-readable storage medium may include, but are not limited to, a floppy disk, a flexible disk, a hard disk, a magnetic tape, other magnetic medium, an application specific integrated circuit (ASIC), a compact disk (CD), other optical medium, a random access memory (RAM), a read only memory (ROM), a memory chip or card, a memory stick, and other media from which a computer, a processor or other electronic device can read.

"Circuit", as used herein, includes but is not limited to hardware, or firmware, or combinations of each to perform a function(s) or an action(s), or to cause a function or action from another logic, circuit, operation, method, or system. Circuit may include a software controlled microprocessor, a discrete logic (e.g., ASIC), an analog circuit, a digital circuit, a programmed logic device, a memory device containing instructions, and other physical devices. Circuit may include one or more gates, combinations of gates, or other circuit components. Where multiple circuits are described, it may be possible to incorporate the multiple circuits into one physical circuit. Similarly, where a single circuit is described, it may be possible to distribute that single circuit between multiple physical circuits.

To the extent that the term "includes" or "including" is employed in the detailed description or the claims, it is intended to be inclusive in a manner similar to the term "comprising" as that term is interpreted when employed as a transitional word in a claim.

Throughout this specification and the claims that follow, unless the context requires otherwise, the words 'comprise' and 'include' and variations such as 'comprising' and 'including' will be understood to be terms of inclusion and not exclusion. For example, when such terms are used to refer to a stated integer or group of integers, such terms do not imply the exclusion of any other integer or group of integers.

To the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

While example systems, methods, and other embodiments have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and other embodiments described herein. Therefore, the invention is not limited to the specific details, the representative apparatus, and illustrative examples shown and described. Thus, this application is intended to embrace alterations, modifications, and variations that fall within the scope of the appended claims.

What is claimed is:

1. A non-transitory computer-readable storage device storing instructions that when executed by a processor control the processor to perform operations, the operations comprising:
   accessing a set of radiological images acquired from a population of subjects, where a member of the set of radiological images includes a left atrium (LA) region;
   constructing a statistical shape differential atlas from the set of radiological images;
   generating a template LA model from the statistical shape differential atlas, where the template LA model includes a site of interest (SOI);
   acquiring a pre-ablation radiological image of a region of tissue in a patient demonstrating atrial fibrillation (AF) pathology;
   generating a patient LA model from the pre-ablation radiological image;
   computing an optimal deformation field that registers the SOI to the patient LA model using a deformable registration approach;
   computing a patient feature vector based on the optimal deformation field;
   generating an AF probability score for the patient based, at least in part, on the patient feature vector;
   generating a classification of the patient based, at least in part, on the AF probability score; and
   displaying the classification or the AF probability score.

2. The non-transitory computer-readable storage device of claim 1, where computing the patient feature vector comprises:
   computing an energy of the optimal deformation field;
   computing a curl of the optimal deformation field; and
   computing a set of first-order statistics based on the energy of the optimal deformation field and the curl of the optimal deformation field.

3. The non-transitory computer-readable storage device of claim 2, where the set of first-order statistics based on the energy of the optimal deformation field and the curl of the optimal deformation field includes: a minimum of the energy, a mean of the energy, a maximum of the energy, or a standard deviation of the energy, and a minimum of the curl, a mean of the curl, a maximum of the curl, or a standard deviation of the curl.

4. The non-transitory computer-readable storage device of claim 1, where the set of radiological images is acquired from a population of patients, where the population includes an AF recurrence positive (AF+) subpopulation, and an AF recurrence negative (AF−) subpopulation; where each member of the set of radiological images includes an atrial mask that defines an LA represented in each member of the set of radiological images, respectively.

5. The non-transitory computer-readable storage device of claim 4, where constructing the statistical shape differential atlas comprises:
   stratifying the set of radiological images into a subset of radiological images associated with a subpopulation of subjects, where a subject belongs to the AF+ subpopulation, or the AF− subpopulation;
   annotating an LA shape for each member of the set of radiological images, respectively;
   defining an LA boundary by transforming the LA shape into a distance transform representation, where the LA boundary defines a volume for the LA shape;
   selecting an AF+ template by selecting a member of the AF+ subpopulation having a median volume for the AF+ subpopulation;

selecting an AF− template by selecting a member of the AF− subpopulation having a median volume for the AF− subpopulation;

generating an AF+ atlas by registering each member of the AF+ subpopulation to the AF+ template; and generating an AF− atlas by registering each member of the AF− subpopulation to the AF− template.

6. The non-transitory computer-readable storage device of claim 5, where generating the AF+ atlas by registering each member of the AF+ subpopulation to the AF+ template comprises:

a first registration of each member of the AF+ subpopulation to the AF+ template using an affine registration, where the transformation parameters of the affine registration are determined using a block matching strategy; and a second registration of each member of the AF+ subpopulation to the AF+ template using a B-spline based non-rigid registration.

7. The non-transitory computer-readable storage device of claim 6, where generating the AF− atlas by registering each member of the AF− subpopulation to the AF− template comprises:

a first registration of each member of the AF− subpopulation to the AF− template using an additional affine registration, where the transformation parameters of the affine registration are determined using an additional block matching strategy; and a second registration of each member of the AF− subpopulation to the AF− template using an additional B-spline based non-rigid registration.

8. The non-transitory computer-readable storage device of claim 7, where generating the template LA model from the statistical shape differential atlas, where the template LA model includes the site of interest (SOI) comprises:

registering the atrial mask of each member of the AF+ subpopulation to the AF− atlas;

identifying a statistically significant shape difference between the AF+ subpopulation and the AF− subpopulation based on the registration of the atrial mask of each member of the AF+ subpopulation to the AF− atlas; and defining the SOI based on the statistically significant shape difference.

9. The non-transitory computer-readable storage device of claim 8, where the statistically significant shape difference is identified using a general linear model (GLM) based t-test framework.

10. The non-transitory computer-readable storage device of claim 1, where a member of the set of radiological images or the pre-ablation radiological image is a non-contrast computed tomography (CT) image, or a contrast enhanced computed tomography angiography (CE-CTA) image.

11. The non-transitory computer-readable storage device of claim 1, where a member of the set of radiological images or the pre-ablation radiological image is a magnetic resonance imaging (MRI) image.

12. The non-transitory computer-readable storage device of claim 1, where generating the AF probability score for the patient based, at least in part, on the patient feature vector comprises:

providing the patient feature vector to a nave Bayes classifier configured to distinguish patient that will experience AF recurrence from a patient that will not experience AF recurrence; and receiving, from the nave Bayes classifier, a probability that the patient will experience AF recurrence.

13. An apparatus comprising:

a memory configured to store a set of computed tomography (CT) images acquired from a population of subjects, where a member of the set of CT images includes a left atrium (LA) region, where the set of CT images is acquired from a population of patients, where the population includes an atrial fibrillation (AF) recurrence positive (AF+) subpopulation, and an AF recurrence negative (AF−) subpopulation; where each member of the set of CT images includes an atrial mask that defines an LA represented in each member of the set of CT images, respectively;

one or more processors configured to:

access the set of CT images;

construct a statistical shape differential atlas from the set of CT images;

generate a template LA model from the statistical shape differential atlas, where the template LA model includes a site of interest (SOI);

acquire a pre-ablation CT image of a region of tissue in a patient demonstrating AF pathology;

generate a patient LA model from the pre-ablation CT image;

compute an optimal deformation field that registers the SOI to the patient LA model using a deformable registration approach;

compute a patient feature vector based on the optimal deformation field;

generate an AF probability score for the patient based, at least in part, on the patient feature vector;

generate a classification of the patient demonstrating AF pathology based, at least in part, on the AF probability score; and display the classification or the AF probability score.

14. The apparatus of claim 13, where computing the patient feature vector comprises:

computing an energy of the optimal deformation field;

computing a curl of the optimal deformation field; and computing a set of first-order statistics based on the energy of the optimal deformation field and the curl of the optimal deformation field.

15. The apparatus of claim 14, where constructing the statistical shape differential atlas comprises:

stratifying set of CT images into a subset of CT images associated with a subpopulation of subjects, where a subject belongs to the AF+ subpopulation, or the AF− subpopulation;

annotating an LA shape for each member of the set of CT images, respectively;

defining an LA boundary by transforming the LA shape into a distance transform representation, where the LA boundary defines a volume for the LA shape;

selecting an AF+ template by selecting a member of the AF+ subpopulation having a median volume for the AF+ subpopulation;

selecting an AF− template by selecting a member of the AF− subpopulation having a median volume for the AF− subpopulation;

generating an AF+ atlas by registering each member of the AF+ subpopulation to the AF+ template; and generating an AF− atlas by registering each member of the AF− subpopulation to the AF− template.

16. The apparatus of claim 15, where generating the AF+ atlas by registering each member of the AF+ subpopulation to the AF+ template comprises:

a first registration of each member of the AF+ subpopulation to the AF+ template using an affine registration, where transformation parameters of the affine registration are determined using a block matching strategy; and a second registration of each member of the AF+ subpopulation to the AF+ template using a B-spline based non-rigid registration.

17. The apparatus of claim 16, where generating the AF− atlas by registering each member of the AF− subpopulation to the AF− template comprises:

a first registration of each member of the AF− subpopulation to the AF− template using an additional affine registration, where the transformation parameters of the affine registration are determined using an additional block matching strategy; and a second registration of each member of the AF− subpopulation to the AF− template using an additional B-spline based non-rigid registration.

18. The apparatus of claim 17, where generating the template LA model from the statistical shape differential atlas, where the template LA model includes the site of interest (SOI) comprises:

registering the atrial mask of each member of the AF+ subpopulation to the AF− atlas;

identifying a statistically significant shape difference between the AF+ subpopulation and the AF− subpopulation based on the registration of the atrial mask of each member of the AF+ subpopulation to the AF− atlas using a general linear model (GLM) based t-test framework; and defining the SOI based on the statistically significant shape difference.

19. The apparatus of claim 13, where generating the AF probability score for the patient based, at least in part, on the patient feature vector comprises:

providing the patient feature vector to a naïve Bayes classifier configured to distinguish a patient that will experience AF recurrence from a patient that will not experience AF recurrence; and receiving, from the naïve Bayes classifier, a probability that the patient will experience AF recurrence.

20. A non-transitory computer-readable storage device storing executable instructions that, in response to execution, cause an atrial fibrillation (AF) recurrence prediction device to perform operations for producing a quantification of differences between a pre-ablation image of a left atrium (LA) and a statistical shape atlas, the operations comprising:

accessing a set of computed tomography (CT) images acquired from a population of subjects, where a member of the set of CT images includes a left atrium (LA) region;

constructing a statistical shape differential atlas from the set of CT images;

generating a template LA model from the statistical shape differential atlas, where the template LA model includes a site of interest (SOI);

acquiring a pre-ablation CT image of a region of tissue in a patient demonstrating AF pathology;

generating a patient LA model from the pre-ablation CT image;

computing an optimal deformation field that registers the SOI to the patient LA model using a deformable registration approach;

computing a patient feature vector based on the optimal deformation field;

generating an AF probability score for the patient based, at least in part, on the patient feature vector;

generating a classification of the patient based, at least in part, on the AF probability score;

generating a personalized AF treatment plan based on the classification, the AF probability score, and the pre-ablation CT image; and displaying the personalized AF treatment plan, the classification, the AF probability score, or the pre-ablation CT image.

* * * * *